(12) United States Patent
Wolfson et al.

(10) Patent No.: US 9,033,989 B2
(45) Date of Patent: May 19, 2015

(54) SURGICAL CUTTING GUIDE

(75) Inventors: David Wolfson, Leeds (GB); Duncan Young, Hebden Bridge (GB); Michael Rock, Leeds (GB); Andrew Bailey, Leeds (GB); Charles Christie, Warsaw, IN (US)

(73) Assignee: DEPUY (IRELAND), Cork (IE)

( * ) Notice: Subject to any disclaimer, the term of this patent is extended or adjusted under 35 U.S.C. 154(b) by 38 days.

(21) Appl. No.: 13/487,601

(22) Filed: Jun. 4, 2012

(65) Prior Publication Data

US 2013/0325045 A1   Dec. 5, 2013

(51) Int. Cl.
*A61B 17/15* (2006.01)
*A61B 17/00* (2006.01)

(52) U.S. Cl.
CPC ............... *A61B 17/155* (2013.01); *A61B 17/15* (2013.01); *A61B 2017/0023* (2013.01)

(58) Field of Classification Search
CPC .............. A61B 17/154; A61B 17/155; A61B 17/15–17/158; A61B 17/1675; A61B 2017/0268; A61B 2017/320052; B23D 51/025
USPC ................................................... 606/86 R–90
See application file for complete search history.

(56) References Cited

U.S. PATENT DOCUMENTS

| | | | | |
|---|---|---|---|---|
| 1,381,033 A * | 6/1921 | Thornton | | 83/762 |
| 1,889,464 A * | 11/1932 | Coble | | 30/372 |
| 2,598,117 A * | 5/1952 | Ethridge | | 269/2 |
| 3,580,472 A * | 5/1971 | Stawski | | 229/122.1 |
| 3,966,337 A * | 6/1976 | Crawford | | 403/170 |
| 4,105,091 A * | 8/1978 | Mahan | | 182/186.5 |
| 4,703,751 A * | 11/1987 | Pohl | | 606/62 |
| 4,718,413 A * | 1/1988 | Johnson | | 606/82 |
| 4,722,330 A * | 2/1988 | Russell et al. | | 606/88 |
| 4,926,847 A | 5/1990 | Luckman | | |
| 5,129,909 A * | 7/1992 | Sutherland | | 606/88 |
| 5,250,050 A * | 10/1993 | Poggie et al. | | 606/79 |
| 5,364,401 A * | 11/1994 | Ferrante et al. | | 606/84 |
| 5,411,505 A * | 5/1995 | Mumme | | 606/88 |
| 5,415,663 A * | 5/1995 | Luckman et al. | | 606/86 R |
| 5,562,675 A * | 10/1996 | McNulty et al. | | 606/96 |
| 5,683,397 A * | 11/1997 | Vendrely et al. | | 606/88 |
| 5,687,628 A * | 11/1997 | Liao | | 83/745 |
| 5,709,689 A * | 1/1998 | Ferrante et al. | | 606/86 R |
| 5,749,876 A * | 5/1998 | Duvillier et al. | | 606/88 |
| 5,897,559 A * | 4/1999 | Masini | | 606/86 R |
| 5,925,049 A * | 7/1999 | Gustilo et al. | | 606/82 |
| 6,007,537 A * | 12/1999 | Burkinshaw et al. | | 606/66 |
| 6,241,733 B1 * | 6/2001 | Nicholson et al. | | 606/84 |
| 6,258,095 B1 * | 7/2001 | Lombardo et al. | | 606/88 |
| 6,344,043 B1 * | 2/2002 | Pappas | | 606/96 |

(Continued)

OTHER PUBLICATIONS

GB 1212943.3 Search Report—Search dated Nov. 20, 2012.

(Continued)

*Primary Examiner* — Michael T Schaper
*Assistant Examiner* — Amy Sipp

(57) ABSTRACT

A surgical cutting guide is described which can guide a cutting implement to cut in a pair of planes at a defined relative orientation. The cutting guide comprises a first plate defining a first cutting plane, a second plate defining a second cutting plane at an angle to the first cutting plane; and a base member to which both the first plate and the second plate are attached. The first and second cutting planes intersect each other at a line of intersection and both the first plate and the second plate extend beyond the line of intersection.

2 Claims, 5 Drawing Sheets

(56) References Cited

U.S. PATENT DOCUMENTS

| | | | |
|---|---|---|---|
| 6,740,092 B2* | 5/2004 | Lombardo et al. | 606/88 |
| 7,674,268 B2* | 3/2010 | Cuckler et al. | 606/86 R |
| 7,901,411 B2* | 3/2011 | Frederick et al. | 606/102 |
| 8,016,833 B2* | 9/2011 | Roger et al. | 606/88 |
| 8,105,353 B2* | 1/2012 | Lebner et al. | 606/215 |
| 8,197,486 B2* | 6/2012 | Oti et al. | 606/87 |
| 8,361,076 B2* | 1/2013 | Roose et al. | 606/88 |
| 8,621,692 B1* | 1/2014 | Kring | 5/658 |
| 8,702,714 B2* | 4/2014 | Martin et al. | 606/88 |
| 8,808,298 B2* | 8/2014 | Raub et al. | 606/88 |
| 8,821,500 B2* | 9/2014 | Roger | 606/88 |
| 8,911,444 B2* | 12/2014 | Bailey | 606/87 |
| 2002/0156479 A1* | 10/2002 | Schulzki et al. | 606/88 |
| 2004/0039396 A1* | 2/2004 | Couture et al. | 606/87 |
| 2004/0153087 A1* | 8/2004 | Sanford et al. | 606/88 |
| 2004/0165369 A1* | 8/2004 | Lionetta et al. | 361/818 |
| 2004/0172502 A1* | 9/2004 | Lionetta et al. | 711/112 |
| 2005/0228393 A1 | 10/2005 | Williams | |
| 2006/0026815 A1* | 2/2006 | Padilla et al. | 29/558 |
| 2006/0278555 A1* | 12/2006 | Langer et al. | 206/523 |
| 2007/0038246 A1* | 2/2007 | Lebner et al. | 606/215 |
| 2007/0162037 A1* | 7/2007 | Chen et al. | 606/87 |
| 2008/0177337 A1* | 7/2008 | McGovern et al. | 606/86 R |
| 2009/0082774 A1 | 3/2009 | Oti | |
| 2010/0168752 A1* | 7/2010 | Edwards | 606/87 |
| 2011/0137316 A1* | 6/2011 | Bhatnagar et al. | 606/88 |
| 2012/0087462 A1* | 4/2012 | Ikhlef | 378/4 |
| 2012/0209276 A1* | 8/2012 | Schuster | 606/88 |
| 2012/0239045 A1* | 9/2012 | Li | 606/88 |
| 2013/0296871 A1* | 11/2013 | Lazar et al. | 606/87 |
| 2013/0325017 A1* | 12/2013 | Lomicka | 606/87 |
| 2014/0257306 A1* | 9/2014 | Edwards et al. | 606/88 |

OTHER PUBLICATIONS

Depuy S-ROM Noiles (RTM) Knee System brochure; Nov. 2010; p. 20; Depuy International Limited, UK.

* cited by examiner

SURGICAL CUTTING GUIDE

TECHNICAL FIELD

The present invention relates to a surgical cutting guide for guiding a cutting implement, such as a saw blade, to cut in a particular plane. In particular, the present invention relates to a cutting guide that can guide a cutting implement to cut in a pair of planes at a defined relative orientation.

BACKGROUND OF THE INVENTION

Surgical cutting guides are used in orthopaedic surgery to prepare bone surfaces to receive an implant. Depending on the nature of the surgery, the cutting guides may have various configurations. In orthopaedic knee surgery, some of the cuts which are required to be made on the femur include chamfer cuts which are made on the anterior and posterior side of the lower extremity of the femur. The two chamfer cuts are made along planes, which intersect at a position away from the lower extremity of the femur.

It is known to provide a combined cutting guide that defines planes for both the chamfer cuts. One such guide is fixed in place on the bone and can guide a cutting implement such as a saw to cut in the two planes required for the two chamfer cuts. For example in the S-ROM (RTM) knee system commercially available from DePuy International Limited, UK, a cutting block is provided which is machined from a solid piece of metal. Slots are machined through the solid block of metal to define the two planes for the chamfer cuts. A disadvantage of such a solid machined block is that it is expensive to produce and therefore not suitable for use as a single use instrument.

It would be desirable to provide a cutting guide with sufficiently low manufacturing cost that it can be provided as a single use instrument, simplifying inventory and removing the requirement to sterilise/decontaminate the instrument between uses.

BRIEF SUMMARY OF THE INVENTION

Accordingly, the present invention provides a surgical cutting guide which comprises first and second plates. Each of the plates defines a separate cutting plane for guiding a cutting implement. Each plate extends either side of a line of intersection of the two cutting plates.

This provides a large surface area to rest a cutting implement, such as a saw blade, and therefore increases the accuracy of the cut in the plane defined by the surface of the plate.

According to a first aspect of the present invention, there is provided a surgical cutting guide comprising:

a first plate defining a first cutting plane;
a second plate defining a second cutting plane at an angle to the first cutting plane; and
a base member to which both the first plate and the second plate are attached; wherein the first and second cutting planes intersect each other at a line of intersection and both the first plate and the second plate extend beyond the line of intersection.

In use, a cutting implement can rest on one of the plates to be guided in the cutting plane defined by the plate. Because the cutting planes extend over the line of intersection they provide a greater surface area for guiding a cutting implement such as a saw. This results in improved accuracy of the cutting implement following the cutting plane defined by each plate. Furthermore, the construction of such a surgical cutting guide is simple, requiring only two plates to define the cutting planes, rather than machining guiding slots in a solid block, and therefore the cost of manufacture is reduced.

Preferably, the first plate and the second plate are interlocked or engaged with each other along the line of intersection.

Preferably, the first plate delimits a first opening;
the second plate delimits a second opening;
at least a portion of the first plate extends through the second opening; and
the first opening is aligned with the second opening along the line of intersection.

This allows a simple construction because the openings enable the plates to intersect in a simple manner. Furthermore, because the first opening is aligned with the second opening along the line of intersection, the openings also ensure that the plates allow passage of a cutting implement along their cutting plane without interfering with the cutting plane of the other plate.

Preferably, the first opening has at least one substantially straight edge which is parallel to the line of intersection and spaced from the second cutting plane. Alternatively, or in addition, it is preferable that the second opening has at least one substantially straight edge which is parallel to the line of intersection and spaced from the first cutting plane. These features provide for captivation of a cutting implement within the cutting guide without requiring additional parts to the plates. The straight edge acts to ensure that the cutting implement remains close to the cutting plate and in the cutting plane defined by the cutting plate. It captivates the cutting implement in the direction perpendicular to the cutting plane, for example it may captivate the cutting implement in the sagittal plane. Therefore the cutting implement follows the cutting plane more easily. This feature requires no additional parts in the construction. A substantially straight edge also allows reciprocation of a cutting implement from side to side along the line of intersection if required.

In one embodiment, the first opening and the second opening are enclosed within the first plate and the second plate respectively. The enclosed openings provide further captivation for a cutting implement. It limits the range of movement of the cutting implement along the line of intersection. Thereby preventing undesirable excursion of the cutting implement. In this case the cutting implement is captivated in a different plane than discussed above.

In an alternate embodiment, the first opening and the second opening both extend to a side of first plate and the second plate, respectively; and at least a portion of the second plate extends through the first opening. In this embodiment, an interdigitated structure is created using openings which extend from the sides of the plate. Such a structure can still provide limits on the movement of a cutting implement along the line of intersection by the gaps between the interdigitated elements.

In another embodiment, the surgical cutting guide may be provided with a first plate and a second plate which have substantially the same shape as each other. This can simplify the manufacture because it is no longer necessary to have different shapes for the first plate and the second plate. For example, in one embodiment the plates may have a general "C"-shaped profile. In another embodiment, the plates may each comprise an opening which extends to one edge. In that case, the openings can be arranged in an interlocking manner, with the first plate arranged to have its opening extending to an edge at an opposite side of the line of intersection to the edge to which the opening of the second plate extends.

Advantageously, at least one of the plates may have an edge portion defining a shape for indicating its position relative to a patient in use. This can simplify orientation of the instrument in use, which is important to ensure that the cuts defined by the two cutting plates are oriented correctly because they may not be symmetrical. It has been found that users generally attempt to match the shape of the instrument to the shape of the anatomy in use. Thus, if the edge profile defines a shape reminiscent of the anatomy, it can indicate the correct orientation relative to that part of the anatomy.

In one embodiment, the edge portion may define a curved surface with a notch. This is visually similar to the intercondylar notch. Preferably, both plates define an edge portion defining a shape for indicating its position relative to a patient in use. In that case, the edge portion of both plates may define a curved surface with a notch and both of these edge portions may be positioned on the posterior side of the plates in use. Alternatively or in addition, another edge portion may define a surface without a notch, which is visually similar to the anterior flange.

The base member may further define an impaction surface and the first opening and the second opening may be each configured to allow access to the impaction surface. In use, it is often necessary to affix the cutting guide to the anatomy. For example, the cutting guide may comprise pins which extend from the base member. To engage these pins with the anatomy, it is necessary to impact the cutting guide against the anatomy. Although this could be carried out by hitting the plates directly, this may damage the construction of the instrument. Providing an opening to allow access to an impaction surface allows use with an impaction instrument without altering the configuration of the plates. Because this is provided by an opening, again, no additional structural members are required.

The base member may comprise a first substantially planar surface, to which the first plate is attached and a second substantially planar surface to which the second plate is attached. The first substantially planar surface and the second substantially planar surface preferably meet at an edge parallel to the line of intersection of the cutting planes. The base member may further comprise a pair of outwardly extending arms positioned opposite each other and extending at least partially in the direction of the line of intersection. These arms may assist in grasping the cutting guide and positioning it prior to use. The base member may also further comprise a third surface for attachment onto a bone.

BRIEF DESCRIPTION OF THE DRAWINGS

Embodiments of the invention will now be defined by way of example only with reference to the accompanying drawings, in which.

Like reference numerals are used throughout this description to indicate like parts.

DETAILED DESCRIPTION OF THE INVENTION

Figure 1:
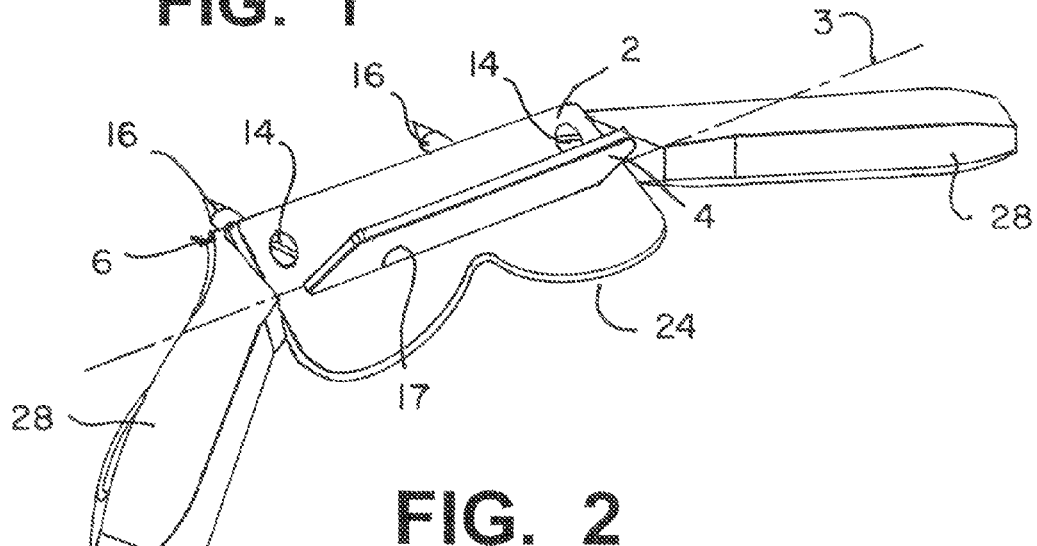
FIG. 1 depicts a perspective view of a first embodiment of a surgical cutting guide according to the present invention.

FIG. 1 depicts a perspective view of a surgical cutting guide according to a first embodiment of the invention. The cutting guide is for use in making anterior and posterior chamfer cuts to the distal femur during total knee replacement surgery. The cutting guide comprises a first plate 2, which defines a cutting plane for making the anterior chamfer cut. A second plate 4 defines a cutting plane for making the posterior chamfer cut. The first plate 2 and the second plate 4 are engaged and to some extent interlocked with each other, as will be explained in more detail below. The first plate 2 and second plate 4 are mounted onto a base member 6, which can be seen most clearly in the exploded views of FIGS. 2 and 3.

In the depicted embodiment, the first plate and second plate are positioned approximately perpendicular with respect to one another. The angle defined by the first plate and the second plate can be varied, however, depending on the chamfer angles needed to prepare the femur to accept the femoral implant. Where the chamfer angle varies from approximately 90 degrees, one skilled in the art will appreciate that the dimensions of the base member and the plate slots might be varied to both permit sufficient clearance for the saw blade to perform the necessary bone cuts and the first plate and second plate to assemble to one another.

Figure 2:
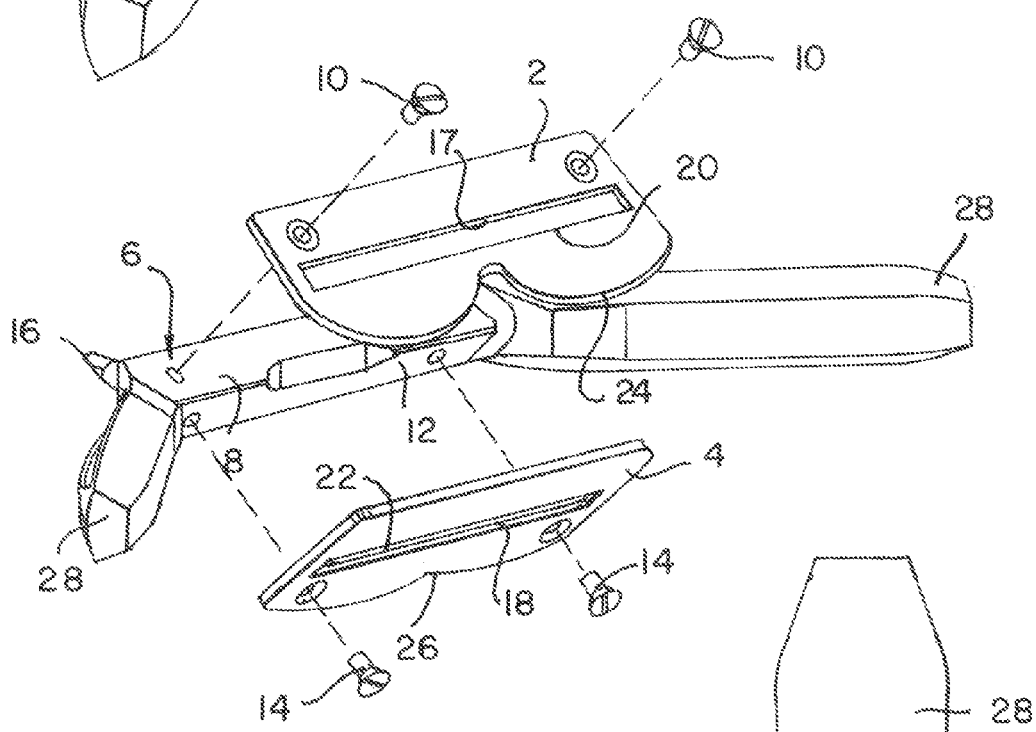
FIGS. 2 and 3 depict exploded views from different viewpoints of the surgical cutting guide of FIG. 1.
Figure 3:
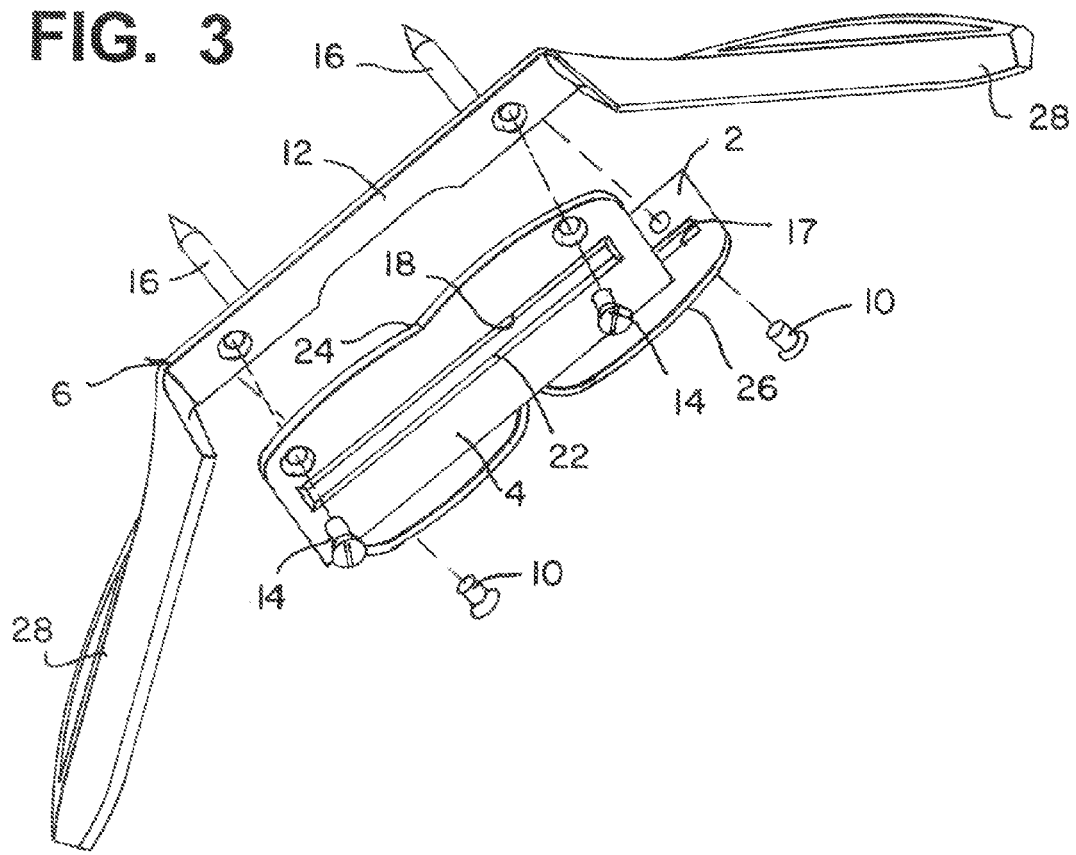

FIG. 2 depicts an exploded view of the surgical cutting guide of FIG. 1 in generally the same orientation as depicted in FIG. 1. FIG. 3 depicts an alternative exploded view from a different orientation, so that the posterior chamfer cutting plane defined by the second plate 4 can be visualised more clearly. Referring to FIGS. 2 and 3, the base member 6 defines a first substantially planar surface 8 onto which the first plate 2 is mounted by mounting screws 10. A second substantially planar surface 12 is also defined by the base member 6. The second cutting plate 4 is mounted onto the second substantially planar surface 12 with mounting screws 14. In alternative embodiments, the plates may be mounted onto the surfaces of the base member 6 in any suitable way, for example with alternative fixations such as a snap-fit, or by using an adhesive.

The two substantially planar surfaces 8, 12 of the base member 6 ensure that the first cutting plate 2 and the second cutting plate 4 are oriented correctly to each other and define the correct angles for the chamfer cuts. In use, the cutting guide is mounted onto a prepared surface of a femoral head with pins 16. When the cutting guide is in place on a distal femur, the base member 6 positions the cutting plates 2, 4 in the correct position for the anterior and posterior chamfer cuts to be made. The cutting guide is therefore a size-specific instrument and a variety of different configurations are possible depending on the size of implant for which the femoral head is being prepared.

As can be seen in FIGS. 2 and 3, the first plate 2 defines an enclosed opening 17 and the second plate 4 defines an enclosed opening 18. The second plate 4 is inserted through the opening 17 of the first plate 2. The dimension of the second plate 4 along the line of intersection 3 of the two cutting planes closely matches, or is slightly smaller, than the dimension of the opening 17 along the line of intersection. As a result, the second plate 4 is partially interlocked with the first plate 2 and cannot move relative to the first plate 2 along the line of intersection 3 of the cutting planes.

Each opening 17, 18 comprises a substantially straight edge 20, 22 which in use is spaced from the line of intersection of the cutting plane. Thus, the combination of the two openings 17 and 18 and the interlocking nature of the first plate 2 and the second plate 4 define two slots for captivating a cutting implement, such as a saw blade, in use.

Both the first plate 2 and the second plate 4 have an edge portion which defines a notched curve profile, indicated at 24 for the first plate 2 and 26 for the second plate 4. This notched curved edge portion mirrors the shape of the intercondylar notch and assists placement of the cutting guide with the correct orientation relative to a femoral head. As can be seen most clearly in FIG. 2, the curved notch surfaces 24, 26 are both located on the posterior side of the cutting guide. Therefore, whichever orientation the cutting guide is viewed, a notched surface is visible indicating which side should be aligned with the posterior.

Outwardly extending arms 28 extend either side of the plates 2, 4 and assist placement of the cutting guide in use.

Figure 4:
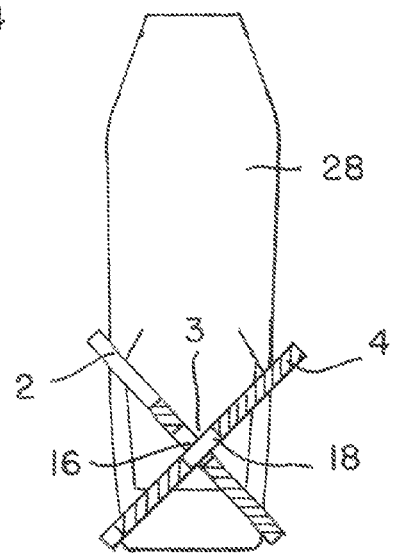
FIG. 4 depicts a section through the centre of the surgical cutting guide of FIG. 1.

The interlocking nature of the plates 2, 4 relative to the base member 6 is illustrated by the cross-section of FIG. 4. This shows how the second plate 4 passes through the opening 17 of the first plate 2. As depicted in FIG. 4, the anterior side is on the right and the posterior side is on the left. The first plate 2 defines the plane for the anterior chamfer cut and the second plate 4 defines the plane of the posterior chamfer cut. As viewed in FIG. 4, the line of intersection 3 of the two cutting planes extends perpendicular to the plane of the cross section.

The plates 2, 4 are preferably manufactured from stainless steel, for example the commercially available steel alloys known as 305 or 17-4. The 17-4 alloy is generally stronger and less susceptible to bending than 305 but is more expensive. The base member 6 is preferably manufactured from a plastics or polymer material, for example injection moulded. For example, the base member 6 may be manufactured from a reinforced polymer, such as a glass reinforced polymer. In one embodiment the base member 6 is made from glass-reinforced polyarylamide, such as that sold under the trade name Ixef and commercially available from Solvay Plastics. The pins 16 are preferably manufactured from a metal or metal alloy, such as stainless steel.

This embodiment provides a surgical cutting guide which can define two intersecting cutting planes with a simple construction and minimal part count. The reduction in part count and ease of construction enable the cost of the instrument to be reduced to a level where a single use instrument is feasible.

Figure 5:
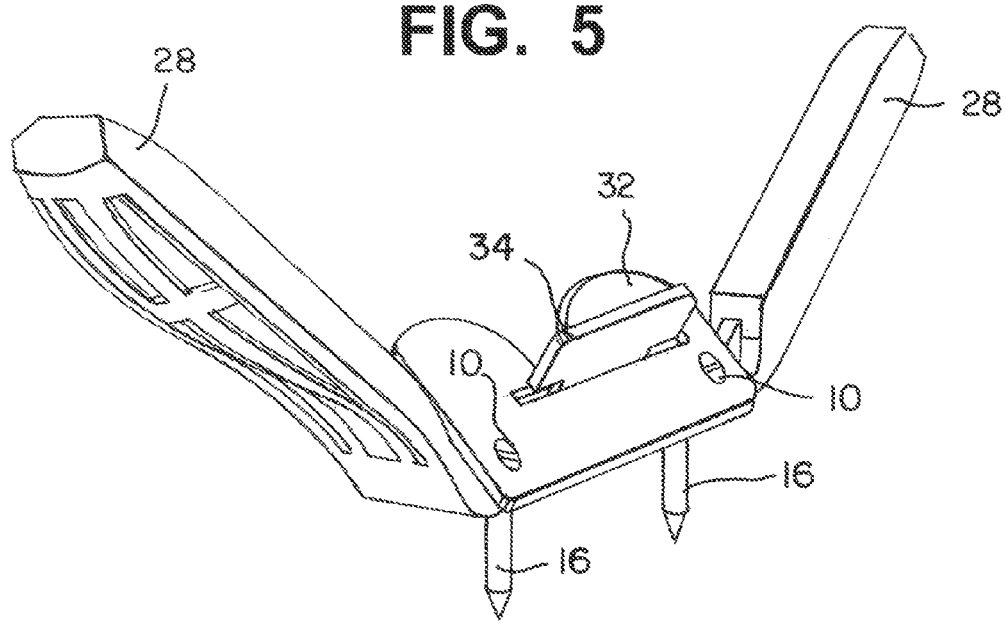
FIG. 5 depicts a perspective view of an alternative embodiment of a surgical cutting guide using interdigitated plates.

A perspective view of an alternative embodiment is depicted in FIG. 5. This embodiment includes an alternative configuration of a first plate 34 and a second plate 32. The first plate 34 defines the anterior cutting plane. The second plate 32 defines the posterior cutting plane. These plates 32, 34 define an opening which is not fully enclosed within either plate 32, 34 and therefore the plates 32, 34 form an interdigitated structure in the assembled cutting guide.

The second plate 32 has a shape reminiscent of the two condyles of the femur, again assisting in orientation. The interdigitated structure is acceptable in this case because two cuts are made to the posterior side.

The construction of this embodiment is otherwise as described for the first embodiment.

Figure 6:
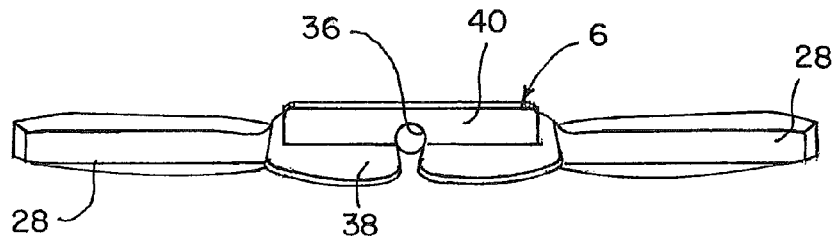
FIG. 6 depicts a top view of a further alternative embodiment in which an access opening is provided to an impaction surface.
Figure 7:
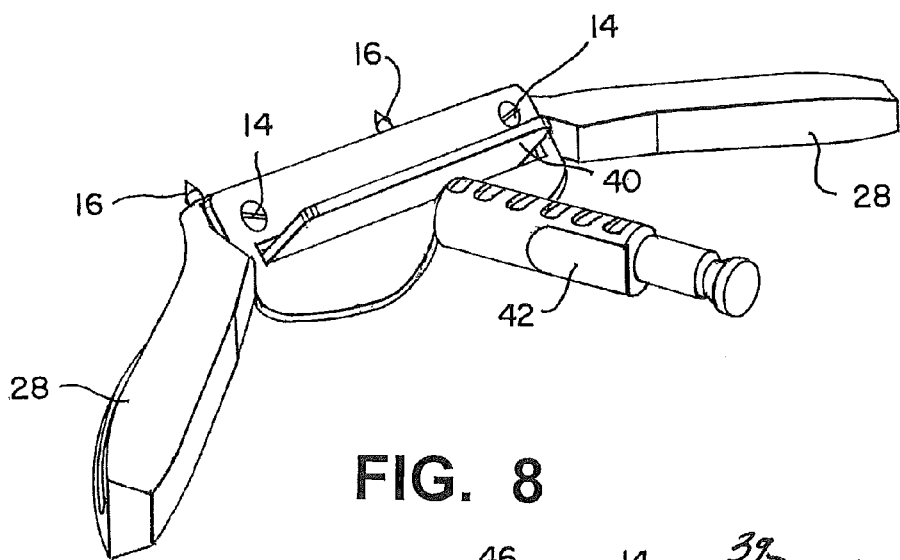
FIG. 7 depicts a perspective view of the surgical cutting guide of FIG. 6 with an impaction instrument in place.

FIG. 6 depicts a modification of the embodiment of FIG. 1 to accommodate an impaction instrument. In this embodiment, the base member 6 is provided with an impaction surface 36 for receiving an impaction instrument. The impaction surface 36 is accessed through an opening provided in both first plate 38 and second plate 40. FIG. 7 depicts a perspective view of the surgical cutting guide with a pin driver 42 engaged with the impaction surface 36. This enables the pin driver 42 to be used to impact the pins 16 into the bone, to ensure that the pins 16 are firmly seated in place with the bone before use. The construction of this embodiment is otherwise the same as the embodiment of FIG. 1.

This embodiment allows the surgical cutting guide to be impacted into place without risk of damaging the first plate 38 or the second plate 40 and the cutting planes they define. This allows the plates 38, 40 to be manufactured from cheaper, less strong alloys because they do not have to deal with impaction forces. For example, it allows reliable construction from softer 305 steel alloy rather than harder, but more expensive, 17-4 steel.

Figure 8:
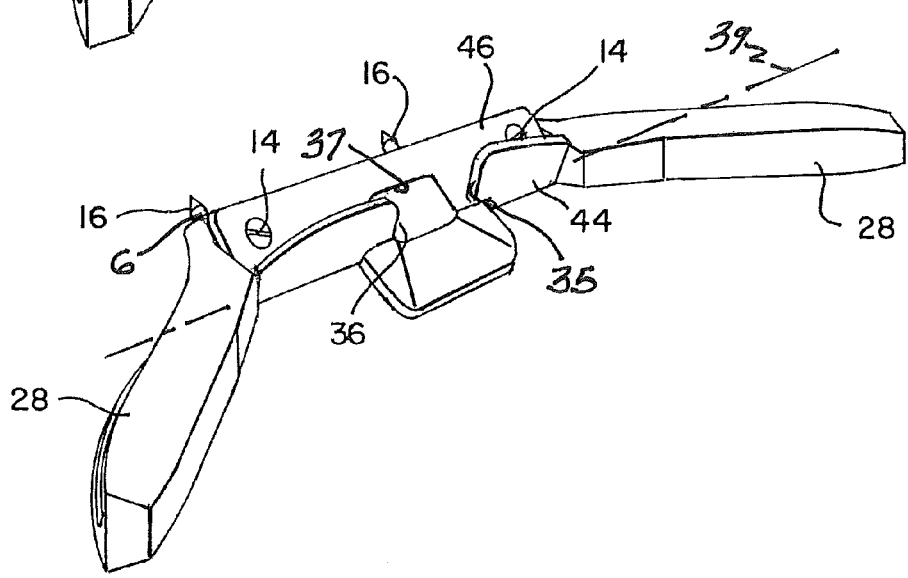
FIG. 8 depicts a perspective view of an alternative embodiment with an opening for an impaction instrument.
Figure 8A:
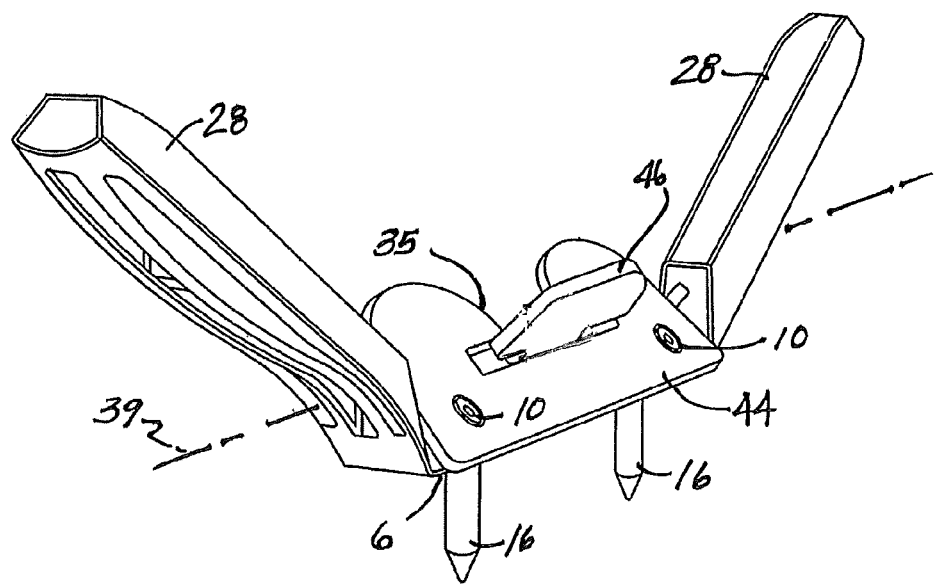
FIG. 8A depicts another perspective view of the embodiment of FIG. 8.
Figure 9:
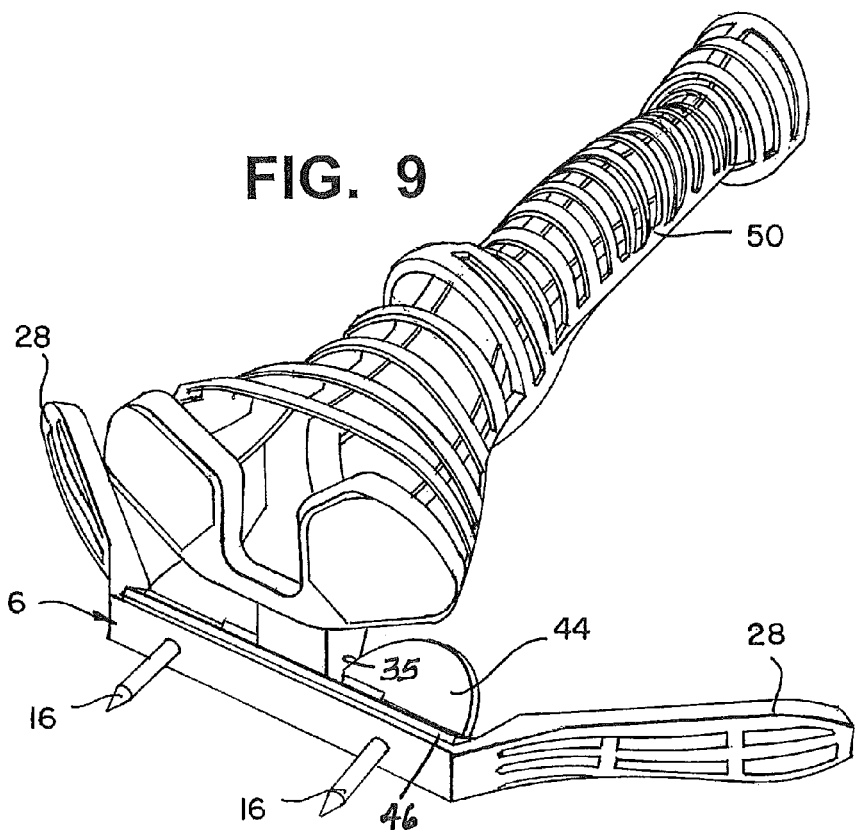
FIG. 9 depicts a perspective view of the cutting guide of FIG. 8 with an impaction instrument attached.

FIGS. 8 and 8A depict perspective views of another embodiment including openings 35, 37 in first plate 44 and second plate 46 to allow access to an impaction surface 36. As there shown, the openings are defined by opposing edges. The construction of this embodiment is the same as the embodiment of FIG. 5, except as described herein. Planes defined by the plates 44, 46 intersect along line of intersection shown at 39 in FIGS. 8 and 8A. In this embodiment, the openings 35, 37 in the plates 44, 46 allow the impaction surface 36 to be engaged by an impactor instrument 50, shown in place in FIG. 9.

Figure 10:
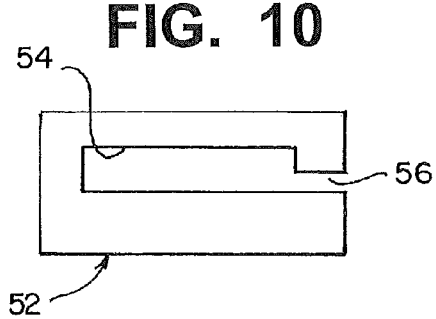
FIG. 10 depicts an example profile for a plate of a further alternative embodiment of the present invention.
Figure 11:
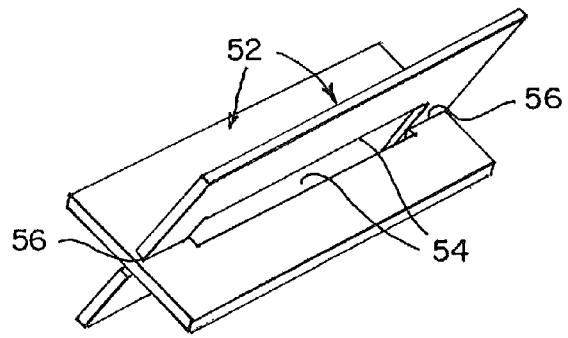
FIG. 11 is a diagrammatic representation of how two plates according to FIG. 10 can be interlocked to form a cutting guide.

A further alternative embodiment is depicted in FIGS. 10 and 11. FIG. 10 depicts a top view of a cutting plate 52 having a general "C" shape and defining an opening 54 which extends to a side of the cutting plate 52. In this embodiment, the shape of cutting plate 52 means that two identical plates can be assembled together so that each plate extends partially into the opening defined by the other plate. The open edge 56 of each plate 52 is then located at opposite sides of a line of intersection. This interlocking arrangement is depicted in perspective view in FIG. 11. This embodiment has the advantage that identical plates 52 can be used, rather than requiring two different shapes of cutting plate as in the above described embodiments.

The depictions in FIGS. 10 and 11 are diagrammatic representations to understand how a cutting guide according to this embodiment could be constructed. For clarity, the base member and pins are not depicted in FIG. 11. The construction of base member and pins is as described above for other embodiments.

Thus, the present invention provides a surgical cutting guide which can be manufactured simply and at low cost, enabling the cutting guide to be provided as a single use instrument.

What is claimed is:

1. A surgical cutting guide for use in cutting part of a bone, the surgical cutting guide comprising:
   a first plate defining a first cutting plane, the first plate having spaced edges defining a first opening;
   a second plate defining a second cutting plane at an angle to the first cutting plane, the second plate having spaced edges defining a second opening; and
   a base member attached to the first plate and the second plate and having a pair of pins extending outwardly from the base member for mounting the surgical cutting guide on the bone;
   wherein the first and second cutting planes intersect one other at a line of intersection and portions of both the first plate and the second plate extend beyond the line of intersection on both sides of the line of intersection, and wherein the first and second plates comprise metal and the base member comprises a different material wherein the first opening is aligned with the second opening along the line of intersection; and wherein at least one of the first opening and the second opening are enclosed within the first plate and the second plate, respectively.

2. A surgical cutting guide for use in cutting part of a bone, the surgical cutting guide comprising:

a first plate defining a first cutting plane, the first plate having spaced edges defining a first opening;

a second plate defining a second cutting plane at an angle to the first cutting plane, the second plate having spaced edges defining a second opening; and a base member attached to the first plate and the second plate and having a pair of pins extending outwardly from the base member for mounting the surgical cutting guide on the bone;

wherein the first and second cutting planes intersect one other at a line of intersection and portions of both the first plate and the second plate extend beyond the line of intersection on both sides of the line of intersection, and wherein the first and second plates comprise metal and the base member comprises a different material; and wherein the base member comprises a first substantially planar surface, to which the first plate is attached and a second substantially planar surface to which the second plate is attached, and wherein the first substantially planar surface and the second substantially planar surface meet at an edge parallel to the line of intersection.

* * * * *